United States Patent [19]
Anton et al.

[11] Patent Number: 5,371,001
[45] Date of Patent: Dec. 6, 1994

[54] ESTERS OF UNSYMMETRICALLY 2-SUBSTITUTED GLYCOLIC ACID DIMERS

[75] Inventors: David L. Anton, Wilmington; Charles E. Nakamura, Claymont, both of Del.

[73] Assignee: E. I. Du Pont de Nemours and Company, Wilmington, Del.

[21] Appl. No.: 85,783

[22] Filed: Jul. 6, 1993

Related U.S. Application Data

[62] Division of Ser. No. 661,776, Feb. 27, 1991, Pat. No. 5,254,718.

[51] Int. Cl.$^5$ ............................................. C12P 7/62
[52] U.S. Cl. ................................................. 435/135
[58] Field of Search ................................... 435/135

[56] References Cited

U.S. PATENT DOCUMENTS

| | | | |
|---|---|---|---|
| 5,004,690 | 4/1991 | Light et al. | 435/135 |
| 5,071,754 | 12/1991 | Walkup et al. | 435/135 |
| 5,156,962 | 10/1992 | Suzuki et al. | 435/135 |
| 5,156,963 | 10/1992 | Eigtved | 435/135 |
| 5,219,733 | 6/1993 | Myojo et al. | 435/135 |
| 5,252,473 | 10/1993 | Walkup et al. | 435/135 |

OTHER PUBLICATIONS

Arie L. Gutman et al., Tetrahedron Lett. 28, 5367 (1987).
Carl A. Elliger et al., J. Agri. Food Chem., 27(3), 527–528 (1979).
Arie L. Gutman et al., J. Org. Chem., 54, 4263 1989.
A. Ajima et al., Biotechnol. Lett., 7, 303 (1985).
Tomoya Kitazume et al., Chem. Express, 3, 135 (1988).
Arie L. Gutman et al., J. Org. Chem., 54, 5645 (1989).
Wallace et al., 198th ACS National Meeting, Miami Beach, Fla., Division of Microbial and Biochemical Technology, Abstracts #91.
D. Klemm et al., Synth. Commun., 18, 2337–2348 (1988).
Iwao Tabushi et al., Tetrahedron Letters, 5, 309–312 (1975).
Ching-Shin Chen et al., Angew Chem. Int. Ed. Engl., 28, 695–707 (1989).
Jonathan S. Dordick, Enzyme Microb. Technol., 11, 194–211 (!989).
I. L. Gatfield, Annals N.Y. Acad. Sci., 434, 569 (1984).
Atushi Makita et al., Tetrahedron Letters, 28, 805 (1987).
Arie L. Gutman et al., Tetrahedron Letters, 28, 3861 (1987).
Wallace, J. S. et al., *Journal of Polymer Science: Part A: Polymer Chemistry, 27, 3271–3284, 1989.*

*Primary Examiner*—C. Warren Ivy
*Assistant Examiner*—A. A. Owens

[57] ABSTRACT

This invention concerns esters of unsymmetrically 2-substituted glycolic acid dimers, a process for their preparation and their use in the preparation of unsymmetrically 3,6-substituted 1,4-dioxane-2,5-diones.

12 Claims, No Drawings

ESTERS OF UNSYMMETRICALLY 2-SUBSTITUTED GLYCOLIC ACID DIMERS

This is a division of Ser. No. 07/661,776, filed on Feb. 27, 1991 now U.S. Pat. No. 5,254,718.

BACKGROUND OF THE INVENTION

1. FIELD OF THE INVENTION

This invention relates to selected esters of unsymmetrically 2-substituted glycolic acid dimers, their use for the preparation of unsymmetrically 3,6-substituted 1,4-dioxane-2,5-diones and a process for their preparation.

2. TECHNICAL REVIEW

Selected esters of unsymmetrically 2-substituted glycolic acid dimers of the general structure:

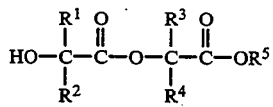

wherein $R^1$, $R^2$, $R^3$, and $R^4$ are selected from the group consisting of H, alkyl, aryl, alkaryl and aralkyl which may include branched chain, unsaturated chain, halogen, nitrile, ketone, and ether substitutions, provided that $R^1$ and $R^2$ are not equal to $R^3$ and $R^4$; and, $R^5$ is selected from the group consisting of alkyl, aryl, alkaryl and aralkyl which may include branched chain, unsaturated chain, halogen, nitrile, and ether substitutions, hereinafter designated as Formula Ia, have been disclosed. While in all of the prior art compounds the pKa of the equivalent alcohol of $R^5$ is greater then 15.5, the compounds claimed in the present invention, hereinafter designated as Formula I, differ from previously disclosed compounds in that the pKa of the equivalent alcohol of $R^5$ is 14.5 or less.

The compounds of the present invention also differ in structure from certain previously disclosed esters of unsymmetrically 2-substituted glycolic acid dimers in that the utility of these previously disclosed dimers resides in a pharmacologically or agriculturally active side group whose activity is modified by the presence of the dimer acid moiety. (See U.S. Pat. Nos. 4,533,659, 4,609,650, 4,663,659, 4,778,809, and JP 50071695) or in a specific use for synthetic organic chemistry, Tetrahedron Lett., 52, 5497–5500 (1982) and Syn. Comm., 18, 2337–2348 (1988).)

Two methods of preparing 2-substituted glycolic acid dimers of Formula Ia are known:

(1) U.S. Pat. No. 4,609,650 discloses the production of selected esters of unsymmetrically 2-substituted glycolic acid dimers (e.g. Formula Ia where $R^1=R^3=R^4=H$, $R^2=CH_2CH(CH_3)_2$, and $R^5=$ a steroid derivative) by reaction of an α-hydroxy carboxylate anion with an ester of an α-halocarboxylic acid derivative. This method suffers from the disadvantage that derivatives of α-halocarboxylic acid are not readily available commercially and usually must be prepared.

(2) Tetrahedron Letters, 5, 309–312, (1975), provides an ester of an unsymmetrically 2-substituted glycolic acid dimer (Formula Ia where $R^1=R^2=R^3=H$, $R^4=CH_2Ph$, and $R^5=CH_3$) by condensation of an α-hydroxy ester derivative with an acid halide derivative bearing a protected hydroxy group. This method is disadvantageous because it requires protection of one of the alcohol moieties, activation of one of the carboxyl groups prior to condensation, and deprotection following condensation.

There is a need for a method for the preparation of esters of unsymmetrically 2-substituted glycolic acid dimers which overcomes the limitations of the described available methods. A method possessing these attributes would be one based on the direct condensation of a mixture of monomers consisting of a compound of Formula III and a compound of Formula IV, as shown in Equation 1, wherein $R^1$, $R^2$, $R^3$, $R^4$ and $R^5$ are as defined on page 1 and $R^6$ is selected from the group including aryl, alkyl, and aralkyl with optional branched chain, halogen, nitrile and ether substitutions.

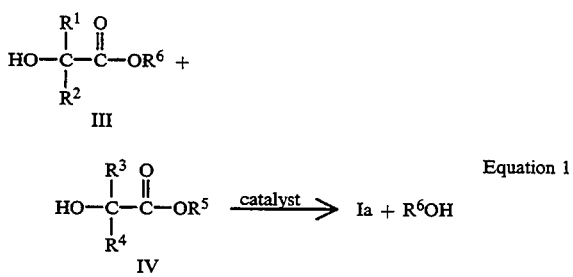

Equation 1

Such a reaction can be catalyzed nonenzymatically (e.g. chemically, by acid or base). However, since both monomers are bifunctional and can act as acyl donor and nucleophile, the expected result would be a mixture of four possible dimers and higher oligomers. For example, if the monomers III and IV are 2-chloroethyl lactate and methyl glycolate, respectively, then the expected dimers would be 2-methoxy-2-oxoethyl lactate, 2-[2-chloroethoxy]-1-methyl-2-oxoethyl lactate, 2-methoxy 2-oxoethyl glycolate and 2-chloroethyl 2-(2-hydroxy-1-oxoethoxy)propionate. Also, higher oligomers would arise from further reaction. Since the relative reactivities of the substrate monomers as acyl donor and as nucleophile is determined by their structure, some degree of selectivity can be achieved when one monomer is a better acyl donor and/or a poorer nucleophile as compared to the other monomer. In practice, high selectivity is difficult to achieve using chemical catalysts and so mixtures are obtained. As such mixtures are difficult to purify, such chemically catalyzed methods, are of limited value.

In contrast to the above described chemical method, a process relying on enzyme catalyzed transesterification of monomer III and monomer IV is much more likely than the above described chemical methods to selectively produce a compound of Formula Ia because the specificity of enzymes toward their substrates is unparalleled by chemical catalysts. In the example cited above, for example, an enzyme catalyzed reaction of 2-chloroethyl lactate and methyl glycolate produces 2-methoxy-2-oxoethyl lactate and no other dimer species or higher oligomer. Thus, a process relying on enzymatic transesterification of monomer III and monomer IV to selectively produce a compound of Formula Ia overcomes the problems inherent in methods utilizing traditional chemical catalysts and offers an attractive alternative to disclosed methods.

The use of enzymes in organic synthesis to effect transesterifications is well documented. For example, the use of lipases has been directed toward resolution of chiral carboxylic acids or alcohols in esterification or transesterification reactions. Angew. Chem. Int. Ed. Engl., 28, 695–707 (1989). Enzyme Microb. Technol. 11, 194–211, (1989).

Enzyme catalyzed reactions of hydroxy-carboxylate esters have been disclosed, however, these reactions have been limited to polymerizations or lactonizations of single substrates. For example, lipase catalyzed formation of lactones or dilactones from ω-hydroxycarboxylic acids and esters or hydroxycarboxylate esters containing secondary alcohols has been described. Annals N.Y. Acad. Sci. 434, 569 (1984); Tetrahedron Lett. 28, 805 (1987); Tetrahedron Lett. 28, 3861 (1987); J. Org. Chem. 54, 4263 (1989). Lipase and protease catalyzed formation of oligomers from carboxylic acids and esters containing a hydroxyl substitution has also been described. Biotechnol. Lett. 7, 303 (1985); Tetrahedron Lett. 28, 5367 (1987); Chem Express 3, 135 (1988); J. Org. Chem. 54, 5645 (1989); Wallace et. al., 198th ACS National Meeting, Miami Beach, Fla., Division of Microbial and Biochemical Technology, Abstract #91.

The enzyme catalyzed reaction of a mixture of dissimilar hydroxycarboxylate esters has not been disclosed in the prior art. Furthermore, the enzyme catalyzed synthesis of unsymmetrically substituted glycolic acid dimer esters has not been disclosed. Indeed, the prior art teaches away from the use of enzymes for the synthesis of unsymmetrically substituted glycolic acid dimer esters by disclosing that, in the presence of enzymes, glycolic acid dimer esters are cleaved by hydrolysis. Synth. Commun. 18, 2337–2348 (1988); Tetrahedron Lett., 5, 309–312 (1975) .

One aspect of the present invention is the use of compounds of Formula Ia as precursors to unsymmetrically 3,6-substituted 1,4-dioxane-2,5-diones of Formula II. The reaction is illustrated in Equation 1:

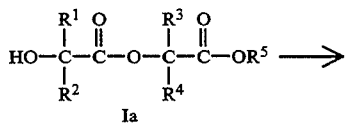
Ia

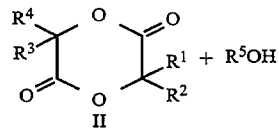
II

Equation 2

None of the above mentioned disclosures have taught that compounds of Formula Ia are useful for the preparation of unsymmetrically 3,6-substituted 1,4-dioxane-2,5diones, represented by Formula II.

SUMMARY OF THE INVENTION

The present invention provides selected novel esters of unsymmetrically substituted glycolic acid dimers represented by the following Formula I,

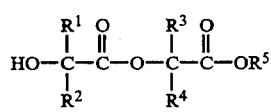
I wherein:

$R^1$, $R^2$, $R^3$ and $R^4$ are selected from the group consisting of hydrogen, alkyl, aryl, alkaryl, aralkyl and optionally containing branched chain, unsaturated chain, halogen, nitrile, ketone and ether substitutions, and wherein $R^1$ and $R^2$ are not equal to $R^3$ and $R^4$.

$R^5$ is selected from the group consisting of alkyl, aryl, alkaryl, and aralkyl, and may, optionally, contain branched chain, unsaturated chain, halogen, nitrile, and ether substitutions, provided that the pKa of the alcohol equivalent of $R^5$ is less than or equal to 14.5. $R^5$ may especially contain substitutions that decrease the leaving ability of the alcohol equivalent of $R^5$.

The present invention further comprises a process for the preparation of compounds of Formula Ia, where Formula Ia is equivalent to Formula I as defined above except that the $pK_a$ limitation on the alcohol equivalent of $R^5$ is removed, wherein a mixture comprising a compound of Formula III and a compound of Formula IV is reacted with an appropriate enzyme, chosen from a group of enzymes including lipases, proteases and esterases, in an appropriate organic solvent. Structures III and IV are shown below:

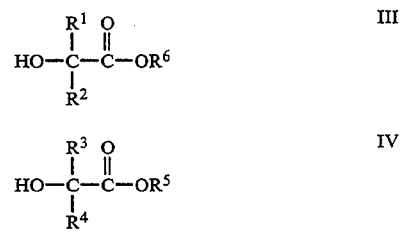

wherein:

$R^1$, $R^2$, $R^3$, $R^4$ and $R^5$ are as defined above in the composition aspect of the present invention, except that the pka limitation of the alcohol equivalent of $R^5$ is removed.

$R^6$ is selected from the group consisting of alkyl aryl and aralkyl and optionally containing branched chain, halogen, nitrile and ether substitutions. $R^6$ may especially contain substitutions (e.g., electron withdrawing substitutions) that enhance the leaving ability of the alcohol equivalent of $R^6$ relative to the leaving ability of the alcohol equivalent of $R^5$.

The present invention also provides a use for compounds of Formula Ia for the preparation of unsymmetrically 3,6-substituted 1,4-dioxane-2,5-diones of Formula II where $R^1$, $R^2$, $R^3$, and $R^4$ are as defined above.

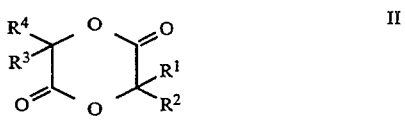
II

Compounds of Formula II are useful because they can be converted to polymers, including homopolymers and copolymers with various lactides, which are useful in the medical field as sutures and bandages because of their compatibility with mammalian tissue, particularly human tissue and their ability to degrade into compatible components which can be absorbed by tissue or excreted. See U.S. Pat. No. 4,033,938, which is incorporated herein by reference.

Accordingly, it is an an object of the present invention to provide a selection of novel esters of unsymmetrically substituted glycolic acid dimers, represented by Formula I. It is a second object of the present invention to provide an efficient synthetic route to compounds represented by Formula Ia relying on the enzymatic transesterification of monomer III and monomer IV to selectively produce compounds of Formula Ia. It is a further object of the above invention to teach the use of compounds of Formula Ia for the preparation of unsymmetrically 3,6-substituted 1,4-dioxane-2,5-diones of Formula II.

DETAILED DESCRIPTION OF THE INVENTION

The present invention provides esters of unsymmetrically substituted glycolic acid dimers represented by Formula I, wherein $R^1$, $R^2$, $R^3$, $R^4$ and $R^5$ are as defined on above, provided that the pKa of the equivalent alcohol of $R^5$ is less than or equal to 14.5.

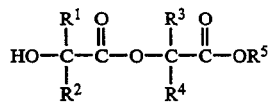

Preferred embodiments for the compositions claimed herein are where $R^1$ is H or $(CH_2)_nCH_3$, where $n=0$ to 3; $R^2$ is H, $(CH_2)_nCH_3$ where $n=0$ to 17, or $(CH_2)_nR$ where n is greater than or equal to 0 and where R may contain branched chain, alkene, alkyne, aryl, alkaryl, ketone, halide and ether substitutions; $R^3$ is H; $R^4$ is H or $(CH_2)_nCH_3$ where $n=0$ to 4; and the alcohol equivalent of $R^5$ is a simple alcohol, provided that the pKa of the equivalent alcohol is less than or equal to 14.5. $R^5$ may be selected from the group including but not limited to phenyl, substituted phenyl, $-CH_2CCl_3$, $-CH_2CF_3$, $-CH_2C\equiv CH$, $-CH_2CH_2F$, and $-CH_2CH_2Cl$. Two embodiments are more preferred: one where $R^1$ is H, $R^2$ is $(CH_2)_nCH_3$ where $n=0-4$ or phenyl, $R^3$ is H, $R^4$ is H and $R^5$ is phenyl; and another where $R^1$, $R^2$, and $R^4 = H$, and $R^3$ is $(CH_2)_nCH_3$ where $n=0-4$ or phenyl and $R^5$ is phenyl.

Compounds of Formula I may be obtained from a chemical process such as that exemplified in Examples 10, 11 and 12. In this process, an ester of an α-bromocarboxylic acid is reacted with the ammonium salt of a carboxylic acid in a solvent such as dimethylformamide to give the corresponding compound of Formula I. Alternatively, compounds of Formula I may be obtained from the novel process, described below and illustrated in Equation 1 above, which relies on the enzymatic transesterification of dissimilar monomers.

This invention also provides an efficient process for the synthesis of novel unsymmetrically substituted glycolic acid dimers compounds represented by Formula Ia, where Formula Ia is equal to Formula I as defined above except that the $pK_a$ limitation on the alcohol equivalent of $R^5$ is removed. In the process a mixture comprising a compound of Formula III and a compound of Formula IV is reacted with an appropriate enzyme, chosen from a group of enzymes including lipases, proteases and esterases, in an appropriate solvent chosen from the group including but not limited to hexane, toluene, dioxane, tetrahydrofuran, ethyl ether, tert-butyl methyl ether and acetonitrile; ethyl ether being preferred. This reaction is illustrated in Equation 1, above. Structures III and IV are shown below:

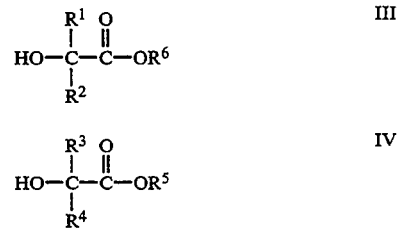

wherein:

$R^1$, $R^2$, $R^3$, $R^4$ and $R^5$ ($R^1$ and $R^2 \neq R^3$ and $R^4$) are as defined above for Formula Ia.

$R^6$ may be selected from the group including, but not limited to, alkyl, aryl and aralkyl and may contain branched chains or unsaturated chains, said chains may contain heteroatom substitutions provided that the substitutions do not interfere with the condensation reaction, and may especially contain substitutions (e.g. electron withdrawing substitutions) that enhance the leaving ability of the alcohol.

The $R^5$ and $R^6$ groups of the ester moieties in structure III and structure IV may be selected from the group including but not limited to phenyl, substituted phenyl, $-CH_2CCl_3$, $-CH_2CF_3$, $-CH_2C\equiv CH$, $-CH_2CH_2F$, $-CH_2CH_2Cl$, $-CH_nCH_3$ where $n=0$ to 7, $-CH(CH_3)_2$, and $-C(CH_3)_3$.

In the operation of the process provided by this invention, esters of unsymmetrically 2-substituted glycolic acid dimers are prepared by combining an appropriate enzyme with a mixture of a compound represented by Formula III and a compound represented by Formula IV in an appropriate organic solvent. Since enzymes are generally not soluble in organic solvents, the reaction mixture is mechanically agitated so that thorough mixing occurs. Mixing of small scale reactions (less than 2L) are conveniently performed on orbital shakers. The reaction is generally performed at room temperature but may be performed in the temperature range of 0°-70° C.

It is important to note that the choice of which compound of Formula III and which compound of Formula IV is used in carrying out the process provided by the present invention is critical. This is because in order for an enzyme to specifically catalyze the formation of a compound of Formula Ia from a mixture of monomers consisting of a compound of Formula III and a compound of Formula IV, the acylating activity of monomer III must be greater than the acylating activity of monomer IV. For a specific enzyme, the acylating activity of Structure III must be functionally defined as being better then the acylating activity of Structure IV when the reaction of enzyme, Structure III and R'OH (a selected alcohol) to form $HOCR^1R^2C(O)OR'$ and $R^6OH$ is faster than the analogous reaction of the enzyme, Structure IV and R'OH to form $HOCR^3R^4C(O)OR'$ and $R^5OH$. These reactions are performed under the conditions of the process of the present invention. For ease of measurement, it is desirable that R'OH be a primary straight chain alcohol that is not equal to $R^6OH$ or $R^5OH$. It is often the case that the order of acylating activity corresponds inversely with the pKa of the alcohol leaving group ($R^5OH$ and $R^6OH$). Additionally, it is useful for the alcohol moiety of monomer IV to be less sterically hindered than the alcohol moiety of monomer III.

The enzymes used herein are selected from a group of enzymes called carboxyesterases and carboxyamidases and include, but are not limited to, lipases, proteases, and esterases. The enzyme preparations may be of varying degrees of purity including crude industrial preparations. These enzymes are generally powders but may be immobilized on solid supports or specifically altered so as to be soluble in organic solvents. Specific powdered enzyme preparations that have been found to be especially useful include Lipase AK, Lipase AP12, Lipase G, Lipase MAP10, Lipase P30, porcine pancreatic lipase, and Protease M. The amount of powdered enzyme used in the reaction will depend upon the specific activity of each particular preparation and the desired time of reaction but will generally be in the range of 10-100 g/L. Powdered enzyme preparations are dried with a vacuum pump for 1-2 days prior to use.

When carrying out the process of the present invention it is sometimes desirable to use an enzyme which is soluble in organic solvents. Enzymes may be specially treated to make them soluble in organic solvents using methods known to those in the art. For example, methods to treat enzymes to enable their dissolution in organic solvents are described by Inada et al. in Biochem. Biophys. Res. Commun. 122, 845 (1984) and Dordick et al. Proc. Natl. Acad. Sci. USA 83, 6255 (1986).

The solvent used in the process of the present invention may be chosen from the group including but not limited to aliphatic hydrocarbons (e.g., hexane and cyclohexane), aromatic hydrocarbons (e.g., benzene and toluene), ethers (e.g., dioxane, tetrahydrofuran, ethyl ether, tert-butyl methyl ether), halogenated hydrocarbons (e.g., methylene chloride and chloroform), nitriles (e.g., acetonitrile), pyridine and dimethylformamide. Ethyl ether has been found to be particularly useful; however, higher boiling ethers are expected to be equally useful. The water content of the solvents are generally low (less than 1%) and the activity of most of the enzymes will be dependent upon the water content. Solvents which cannot be used herein include water, alcohols and esters which are substrates of the enzymes.

The ratio of the two substrate monomers are generally in the range from 1:1 to 1:2 but may be as much as 1:10. Useful ranges of total substrate concentration are expected to be from 100 mM to neat.

The reaction is terminated by filtration. The enzyme may be recovered and reused. Product is obtained from the filtered reaction mixture by common purification procedures such as chromatography on silica. In some cases distillation of excess monomer is useful.

Finally, this invention provides for the use of compounds of Formula Ia, where Formula Ia is equivalent to Formula I as defined above except that the $pK_a$ limitation on the alcohol equivalent of $R^5$ is removed, for the production of unsymmetrically 3,6-substituted 1,2-dioxane-2,5 diones of Formula II where $R^1$, $R^2$, $R^3$, and $R^4$ are as defined above. In the use aspect of this invention, $R^5$ may be selected from the group including but not limited to phenyl, substituted phenyl, $—CH_2CCl_3$, $—CH_2CF_3$, $—CH_2C\equiv CH$, $—CH_2CH_2F$, $—CH_2CH_2Cl$, $—CH_nCH_3$ where n=0 to 7, $—CH(CH_3)_2$, and $—C(CH_3)_3$.

In carrying out this aspect of the present invention, compounds of Formula Ia may be converted to compounds of Formula II, as shown in Equation 2, by heating in an aromatic hydrocarbon solvent in the presence of an organic acid. For example, Illustrative Example 1 describes the conversion of 2-methoxy-2 oxoethyl lactate to 3-methyl-1,4-dioxane-2,5-dione by heating in toluene in the presence of a catalytic amount of (1s)-(+)-10-camphor-sulphonic acid.

EXAMPLES

Crude enzyme preparations were purchased as powders from Amano International Enzyme Co., Inc., Troy, Va. 22974 (Lipase AK, Lipase AP12, Lipase G, Lipase MAP10, Lipase P30, Protease M) or Sigma Chemical Co., St. Louis, Mo. 63178 (porcine pancreatic lipase).

Enzyme reactions were initiated by the addition of the substrates (made up in appropriate solvents and usually containing 0.125% tert-butylbenzene as internal standard) to the enzyme powder which had been dried under vacuum for 24-48 hr. The reactions were performed in closed containers at room temperature and were mechanically agitated so that the insoluble enzyme powder remained in suspension. The progress of the reaction was monitored by gas chromatography (GC) using a polyethylene glycol capillary column (Method A) or a methylsilicone capillary column (Method B).

NMR spectra were obtained in $CDCl_3$ using a General Electric QE-300 MHz spectrometer. Chemical shifts are reported as ppm downfield from an internal tetramethylsilane standard. High resolution mass spectral (HRMS) data were obtained using a VG Micromass 7070 high resolution mass spectrometer coupled to a Varian Vista 6000 capillary gas chromatograph. Where appropriate, HRMS samples were trimethylsilated using N-methyl-N-(trimethylsilyl)-trifluoroacetamide. Flash chromatography was performed using 230-400 mesh silica gel. Boiling points and melting points were not corrected.

Tables I and II summarize the $R^1$, $R^2$, $R^3$, $R^4$ and $R^5$ substituent structures in formula II.

TABLE I

| (Enzymatic Synthesis) | | | | | |
|---|---|---|---|---|---|
|  | $R^1$ | $R^2$ | $R^3$ | $R^4$ | $R^5$ |
| Example 1 | H | $CH_3$ | H | H | $CH_3$ |
| Example 2 | H | $CH_3$ | H | H | $CH(CH_3)_2$ |
| Example 3 | $CH_3$ | $CH_3$ | H | H | $CH_3$ |
| Example 4 | H | $CH_2CH_3$ | H | H | $CH_3$ |
| Example 5 | $CH_3$ | $CH_2CH_3$ | H | H | $CH_3$ |
| Example 6 | H | $CH(CH_3)_2$ | H | H | $CH_3$ |
| Example 7 | H | Ph | H | H | $CH(CH_3)_2$ |
| Example 8 | $CH_3$ | Ph | H | H | $CH(CH_3)_2$ |
| Example 9 | H | $CH_2Ph$ | H | H | $CH(CH_3)_2$ |

TABLE II

| (Chemical Synthesis) | | | | | |
|---|---|---|---|---|---|
|  | $R^1$ | $R^2$ | $R^3$ | $R^4$ | $R^5$ |
| Example 10 | H | $CH_3$ | H | H | $CH_3$ |
| Example 11 | H | $CH_3$ | H | H | Ph |
| Example 12 | H | H | $CH_3$ | H | $CH_3$ |

Illustrative Example 1

Synthesis of 3-methyl-1,4-dioxane-2,5-dione

2-Methoxy-2-oxoethyl lactate (123 mg, 0.76 mmol), prepared as described in Example 1, was added to 25 mL of refluxing toluene containing (1S)-(+)-10-camphor-sulfonic acid (8.8 mg, 0.038 mmol). The refluxing toluene was made to pass through ca. 8 mL of crushed molecular sieves (type 4A) before returning to the reaction vessel. After 6 hr, the reaction mixture was cooled to room temperature, applied to a 40 mL silica gel column equilibrated in toluene and eluted with ethyl acetate. The ethyl acetate was evaporated and the title compound was identified as a component of the recovered material by GC (Method A) and GC/MS: HRMS calcd for $C_5H_6O_4$ 130.0266, obsd 130.0265.

Example 1a

Synthesis of 2-methoxy-2-oxoethyl lactate

Step 1: Lactic acid (74 mL of an 85% aqueous solution, 0.84 mol) and freshly distilled 2-chloroethanol (670 mL, 10.0 mol) were refluxed with 400 mL of toluene and 0.4 mL of conc. $H_2SO_4$ until one equivalent of $H_2O$ was collected in a Dean-Stark trap. The reaction mixture was cooled to room temperature, diluted with ethyl ether, and washed with a $NaHCO_3/NaCl$ solution. The organic phase was dried with $MgSO_4$, solvent was removed under reduced pressure, and the residue was distilled at 10 mm Hg. A fraction recovered at 95°–100° C./10 mm Hg was redistilled to give 2-chloroethyl lactate as a clear colorless liquid (76.7 g, 60%): b.p. 95° C./10 mm Hg; $^1$H NMR $\delta$1.46 (d, 3H, J=6.9 Hz), $\delta$2.95 (bs, 1H), $\delta$3.72 (t, 2H, J=5.6 Hz), $\delta$4.35 (q, 1H, J=6.9 Hz), $\delta$4.44 (m, 2H); $^{13}$C NMR 20.4, 41.2, 64.8, 66.8, 175.2 ppm; HRMS calcd for $C_4H_5ClO_3$Tms (M-CH$_3$) 209.0401, obsd 209.0392.

Step 2: 2-Chloroethyl lactate (19.10 g, 0.125 mol) and methyl glycolate (11.26 g, 0.125 mol) in 250 mL of ethyl ether containing 0.125% tert-butylbenzene was added to 17.5 g Lipase P30 powder in duplicate reactions. The reaction mixtures were agitated on an orbital shaker (175 RPM) at room temperature for 8 hr and an additional equivalent of methyl glycolate was added. After agitation for a further 40 hr, the enzyme powders were removed by filtration and the filtrates were combined and evaporated. The resulting residue was chromatographed by flash chromatography (ethyl acetate/hexane, 22.5/77.5) to give the title compound as an oil (6.00 g, 15%- an approximately equal amount of product was recovered in fractions which also contained methyl glycolate): $^1$H NMR $\delta$1.49 (d, 3H, J=7.0 Hz), $\delta$3.55 (bs, 1H), $\delta$3.78 (s, 3H), $\delta$4.43 (q, 1H, J=6.9 Hz), $\delta$4.67 (d, 1H, J=15.9 Hz), $\delta$4.76 (d, 1H, J=15.9 Hz); $^{13}$C NMR 20.04, 52.09, 60.87, 66.67, 167.63, 174.62; HRMS calcd for $C_5H_6O_5$Tms (M-CH$_3$) 219.0688, obsd 219.0641.

Example 1b

Synthesis of 2-methoxy-2-oxoethyl lactate

A 6.5 mL aliquot of an ethyl ether solution containing 0.25M 2-chloroethyl lactate (prepared as described in Example 1a), 0.25M methyl glycolate, and 0.125% tert-butylbenzene was added to 0.5 g Lipase P30. After mixing for 48 hr at room temperature, the conversion of 2-chloroethyl lactate to the title compound was estimated (by GC, Method A) to be 40%. In identical reactions substituting Lipase AK, Lipase G, Lipase MAP10, Protease M, Lipase AP12, or porcine pancreatic lipase for Lipase P30, the relative values for conversions at 48 hr (Lipase P30=100) were 101, 90, 44, 43, 32, and 13, respectively.

Example 2

Synthesis of 2-(1-methylethoxy)-2-oxoethyl lactate

2-Chloroethyl lactate (1.91 g, 12.5 mmol) and various amounts of isopropyl glycolate (1.48, 2.22 and 2.95 g; 12.5, 18.8 and 25.0 mmol, respectively) in 25 mL of ethyl ether containing 0.125% tert-butylbenzene were added to 1.75 g Lipase P30 powder and the reaction mixtures were agitated on an orbital shaker (175 RPM) at room temperature for 48 hr. After 48 hr, conversion of 2-chloroethyl lactate to the title compound was estimated (by GC, Method A) to be 30, 38 and 44% with 1.0, 1.5 and 2.0 equivalents of isopropyl glycolate, respectively. The GC peak assigned to the title compound was confirmed by HRMS: calcd for $C_7H_{10}O_5$Tms (M-CH$_3$) 247.1001, obsd 247.0990. A portion of one of the reactions was partially purified by flash chromatography (ethyl acetate/hexane, 20/80) to give a mixture of 2-chloroethyl lactate and the title compound. The partially purified mixture was separated by flash chromatography ($CH_2Cl_2$/isopropanol, 99/1) to give the title compound: $^1$H NMR $\delta$1.27 (d, 6H, J=6.3 Hz), $\delta$1.49 (d, 3H, J=7.0 Hz), $\delta$3.28 (d, 1H, J=4.6 Hz), $\delta$4.42 (m, 1H), $\delta$4.60 (d, 1H, J=15.8 Hz),$\delta$4.71 (d, 1H, J=15.8 Hz), $\delta$5.09 (m, 1H, J=6.3 Hz); $^{13}$C NMR 20.3, 21.7, 61.5, 66.9, 69.6, 166.8, 174.9.

The efficacy of various enzyme preparations to catalyze the conversion of 0.25M 2-chloroethyl lactate and 0.25M isopropyl glycolate in ethyl ether to the title compound was determined after reaction for 24 hr with 0.5 g enzyme per 6.5 mL reaction mixture. Substituting Lipase AK, porcine pancreatic lipase, Lipase MAP10, Protease M, Lipase AP12, or Lipase G for Lipase P30, the relative values for conversion (Lipase P30=100) were 104, 44, 40, 36, 29 and 26, respectively. In each case substitution of acetonitrile for ethyl ether resulted in a slight reduction in the rate of reaction.

Example 3a

Synthesis of 2-methoxy-2-oxoethyl 2-hydroxy-2-methylpropionate

Step 1: 2-Chloroethyl 2-hydroxy-2-methylpropionate was prepared from 2-hydroxy-2-methylpropionic acid and excess 2-chloroethanol essentially by the method described in Step 1 of Example 1: b.p. 75°–77° C./6 mm Hg; $^1$H NMR $\delta$1.47 (s, 6H), $\delta$3.18 (s, 1H), $\delta$3.72 (t, 2H, J= 5.6 Hz), $\delta$4.43 (t, 2H, J=5.6 Hz); $^{13}$C NMR 27.1, 41.2, 64.8, 72.1, 176.8 ppm; HRMS calcd for $C_5H_7ClO_3$Tms (M-CH$_3$) 223.0557, obsd 223.0577.

Step 2: A 6 mL aliquot of an ethyl ether solution containing 0.25M 2-chloroethyl 2-hydroxy-2-methylpropionate, 0.25M methyl glycolate, and 0.125% tert-butylbenzene was added to 0.5 g Lipase P30. After mixing for 48 hr at room temperature, the conversion of 2-chloroethyl 2-hydroxy-2-methylpropionate to the title compound was estimated (by GC, Method A) to be 47%. The GC peak assigned to the title compound was confirmed by HRMS: calcd for $C_6H_{10}O_5$Tms (M-CH$_3$) 233.0845, obsd 233.0870. In identical reactions substituting Lipase AK, Lipase MAP10, Lipase G, Lipase AP12, Protease M, or porcine pancreatic lipase for Lipase P30, the relative values for conversions at 48 hr (Lipase P30=100) were 33, 32, 16, 14, 13 and 2, respectively.

Example 3b

Synthesis of 2-methoxy-2-oxoethyl 2-hydroxy-2-methylpropionate

2-Chloroethyl 2-hydroxy-2-methylpropionate, prepared as described in Step 1 of Example 3a, (5.22 g, 31.3 mmol) and methyl glycolate (2.83 g, 31.4 mmol) in 125 mL of ethyl ether containing 0.125% tert-butylbenzene was added to 9.0 g Lipase P30 and the reaction mixture was agitated on an orbital shaker for 4d. The enzyme powder was removed by filtration, the solvent was removed, and a portion of the resulting residue was purified by flash chromatography (ethyl acetate:hexane, 20/80) to give the title compound as an oil: $^1$H NMR $\delta$1.51 (s, 6H), $\delta$3.14 (s, 1H), $\delta$3.78 (s, 3H), $\delta$4.71 (s, 2H); $^{13}$C NMR 27.0, 52.1, 61.1, 72.1, 167.6, 176.4 ppm.

Example 4

Synthesis of 2-methoxy-2-oxoethyl 2-hydroxybutyrate

Step 1: The sodium salt of D,L-2-hydroxybutyric acid (15 g, 0.12 mol) was dissolved in 30 mL H$_2$O, titrated to pH 1 with 6N HCl, saturated with NaCl and the aqueous solution was extracted with ethyl ether to give 12.4 g of D,L-2-hydroxybutyric acid. 2-Chloroethyl 2-hydroxybutyrate was prepared from D,L-2-hydroxybutyric acid and excess 2-chloroethanol essentially by the method described in Step 1 of Example 1: b.p. 115° C./25 mm Hg; $^1$H NMR $\delta$0.99 (t, 3H, J=7.5 Hz), $\delta$ca. 1.74 (m, 1H), $\delta$ca. 1.88 (m, 1H), $\delta$2.88 (bs, 1H), $\delta$3.72 (t, 2H, J=5.6), $\delta$4.22 (dd, 1H, J=4.5 and 6.7 Hz), $\delta$4.36–4.52 (m, 2H); HRMS calcd for C$_5$H$_7$ClO$_3$Tms (M-CH$_3$) 223.0557, obsd 223.0577.

Step 2: A 6 mL aliquot of an ethyl ether solution containing 0.25M 2-chloroethyl 2-hydroxybutyrate, 0.25M methyl glycolate, and 0.125% tert-butylbenzene was added to 0.43 g Lipase AK. After mixing for 48 hr at room temperature, the conversion of 2-chloroethyl 2-hydroxybutyrate to the title compound was estimated (by GC, Method A) to be 43%. The GC peak assigned to the title compound was confirmed by HRMS: calcd for C$_6$H$_8$O$_5$Tms (M-CH$_3$) 233.0845, obsd 233.0878. In identical reactions substituting Lipase P30, Lipase G, or porcine pancreatic lipase for Lipase AK, the relative values for conversions at 48 hr (Lipase AK=100) were 81, 71, and 48, respectively.

Example 5

Synthesis of 2-methoxy-2-oxoethyl 2-hydroxy-2-methylbutyrate

Step 1: 2-Chloroethyl 2-hydroxy-2-methylbutyrate was prepared from 2-hydroxy-2-methylbutyric acid and excess 2-chloroethanol essentially by the method described in Step 1 of Example 1: b.p. 108° C./20 mm Hg; $^1$H NMR $\delta$0.90 (t, 3H, J=7.4 Hz), $\delta$1.44 (s, 3H), $\delta$ca. 1.70 (m, 1H), $\delta$ca. 1.83 (m, 1H), $\delta$3.10 (s, 1H), $\delta$3.72 (t, 2H, J=5.6 Hz), $\delta$4.43 (dd, 2H, J=5.6 Hz and 1.5 Hz); HRMS calcd for C$_6$H$_9$ClO$_3$Tms (M-CH$_3$) 237.0714, obsd 237.0750.

Step 2: A 6 mL aliquot of an ethyl ether solution containing 0.25M 2-chloroethyl 2-hydroxy-2-methylbutyrate, 0.25M methyl glycolate, and 1.0% tert-butylbenzene was added to 0.4 g Lipase P30. After mixing for 7 d at room temperature, the conversion of 2-chloroethyl 2-hydroxy-2-methylbutyrate to the title compound was estimated (by GC, Method A) to be approximately 10%. The GC peak assigned to the title compound was confirmed by HRMS: calcd for C$_7$H$_{10}$O$_5$Tms (M-CH$_3$) 247.1001, obsd 247.0998. In identical reactions substituting Lipase MAP10, Lipase G, Lipase AK, or porcine pancreatic lipase for Lipase P30, the relative values for conversions at 7 d (Lipase P30=100) were 73, 21, 16, and 0, respectively.

Example 6

Synthesis of 2-methoxy-2-oxoethyl 2-hydroxy-3-methylbutyrate

Step 1: 2-Chloroethyl 2-hydroxy-3-methylbutyrate was prepared from 2-hydroxy-3-methylbutyric acid and excess 2-chloroethanol essentially by the method described in Step 1 of Example 1: b.p. 137° C./20 mm Hg; $^1$H NMR $\delta$0.90 (d, 3H, J=6.9 Hz), $\delta$1.04 (d, 3H, J=6.9 Hz), $\delta$2.12 (dqq, 1H, J=3.6, 6.9, 6.9 Hz), $\delta$2.76 (d, 1H, J=6.4 Hz), $\delta$3.72 (t, 2H, J=5.6 Hz), $\delta$4.10 (dd, 1H, J=3.6 Hz, 6.3 Hz), $\delta$4.36–4.53 (m, 2H); HRMS calcd for C$_6$H$_9$ClO$_3$Tms (M-CH$_3$) 237.0714, obsd 237.0677.

Step 2: A 6 mL aliquot of an ethyl ether solution containing 0.25M 2-chloroethyl 2-hydroxy-3-methylbutyrate, 0.25M methyl glycolate, and 1.0% tert-butylbenzene was added to 0.40 g Lipase P30. After mixing for 10 d at room temperature, the conversion of 2-chloroethyl 2-hydroxy-3-methylbutyrate to the title compound was estimated (by GC, Method A) to be <20%. The GC peak assigned to the title compound was confirmed by HRMS: calcd for C$_7$H$_{10}$O$_5$Tms (M-CH$_3$) 247.1001, obsd 247.0973. In identical reactions substituting Lipase AK or porcine pancreatic lipase for Lipase P30, the relative values for conversions at 10 d (Lipase P30=100) were 33 and 0, respectively.

Example 7

Synthesis of 2-(1-methylethoxy)-2-oxoethyl 2-hydroxy-2-phenylacetate

Step 1: 2-Chloroethyl 2-hydroxy-2-phenylacetate was prepared from 2-hydroxy-2-phenylacetic acid and excess 2-chloroethanol essentially by the method described in Step 1 of Example 1; however, the distillate solidified after standing at 4° C.: b.p. 119° C./0.35 mm Hg; m.p. 43°–45° C.; $^1$H NMR $\gamma$3.50 (d, 1H, J=6.0 Hz), $\gamma$3.58–3.62 (m, 2H), $\gamma$4.28–4.46 (m, 2H), $\gamma$5.22 (d, 1H, J=5.9 Hz), $\delta$7.3–7.4 (5H); HRMS calcd for C$_9$H$_7$ClO$_3$Tms (M-CH$_3$) 271.0557, obsd 271.0598.

Step 2: A 6 mL aliquot of an ethyl ether solution containing 0.25M 2-chloroethyl 2-hydroxy-2-phenylacetate, 0.25M isopropyl glycolate, and 1.0% tert-butylbenzene was added to 0.43 g Lipase P30. After mixing for 5 d at room temperature, the conversion of 2-chloroethyl 2-hydroxy-2-phenylacetate to the title compound was estimated (by GC, Method B) to be approximately 15%. The GC peak assigned to the title compound was confirmed by HRMS: calcd for C$_{12}$H$_{12}$O$_5$Tms (M-CH$_3$) 309.1158, obsd 309.1171. In identical reactions substituting Lipase G, Lipase AK, Lipase MAP10, Protease M, Lipase AP12, or porcine pancreatic lipase for Lipase P30, the relative values for conversions at 5 d (Lipase P30=100) were 17, 12, 12, 6, 4, and 2%, respectively.

Example 8

Synthesis of 2-(1-methylethoxy)-2-oxoethyl 2-hydroxy-2-phenylpropionate

Step 1: 2-Chloroethyl 2-hydroxy-2-phenylpropionate was prepared from 2-hydroxy-2-phenylpropionic acid hemihydrate and excess 2-chloroethanol essentially by the method described in Step 1 of Example 1: $^1$H NMR δ1.81 (s, 3H), δ3.63-3.68 (m, 2H), δ3.72 (s, 1H), δ4.32-4.48 (m, 2H), δ7.2-7.6 (5H); HRMS calcd for $C_{10}H_9ClO_3$Tms (M-CH$_3$) 285.0714, obsd 285.0764.

Step 2: A 4.5 mL aliquot of an ethyl ether solution containing 0.25M 2-chloroethyl 2-hydroxy-2-phenylpropionate, 0.25M isopropyl glycolate, and 1.0% tert-butylbenzene was added to 0.30 g Lipase P30. After mixing for 8 d at room temperature, the conversion of 2-chloroethyl 2-hydroxy-2-phenylpropionate to the title compound was estimated (by GC, Method B) to be approximately 10%. The GC peak assigned to the title compound was confirmed by HRMS calcd for $C_{13}H_{14}O_5$Tms (M-CH$_3$) 323.1314, obsd 323.1366.

Example 9a

Synthesis of 2-(1-methylethoxy)-2-oxoethyl 2-hydroxy-3-phenylpropionate

Step 1: 2-Chloroethyl 2-hydroxy-3-phenylpropionate was prepared from (S)-2-hydroxy-3-phenylpropionic acid and excess 2-chloroethanol essentially by the method described in Step 1 of Example 1; however, the distillate solidified after standing at 4° C.: b.p. 120° C./0.35 mm Hg; $^1$H NMR δ2.86 (bs, 1H), δ2.98 (dd, 1H, J=6.7 Hz and 14.0 Hz), δ3.13 (dd, 1H, J=4.6 Hz and 14.0 Hz), δ3.63 (t, 2H, J=5.6 Hz), δ4.35 (m, 2H), δ4.48 (dd, 1H, J=4.7 Hz and 6.6 Hz), δ7.2-7.3 (5H); $^{13}$C NMR 40.5, 41.0, 64.8, 71.3, 126.8, 128.3, 129.4, 136.2, 173.6 ppm; HRMS calcd for $C_{10}H_9ClO_3$Tms (M-CH$_3$) 285.0714, obsd 285.0756.

Step 2: A 6 mL aliquot of an ethyl ether solution containing 0.25M 2-chloroethyl 2-hydroxy-3-phenylpropionate, 0.25M isopropyl glycolate, and 1.0% tert-butylbenzene was added to 0.43 g Lipase AK. After mixing for 2 d at room temperature, the conversion of 2-chloroethyl 2-hydroxy-3-phenylpropionate to the title compound was estimated (by GC, Method B) to be approximately 28%. The GC peak assigned to the title compound was confirmed by HRMS: calcd for $C_{13}H_{14}O_5$Tms (M-CH$_3$) 323. 1314, obsd 323. 1290. In identical reactions substituting Lipase P30, Lipase G, Lipase MAP10, porcine pancreatic lipase, Lipase AP12 or Protease M for Lipase AK, the relative values for conversions at 2 d (Lipase AK=100) were 88, 85, 76, 51, 7, and 7%, respectively.

Example 9b

Synthesis of 2-(1-methylethoxy)-2-oxoethyl 2-hydroxy-3-phenylpropionate

2-Chloroethyl 2-hydroxy-3-phenylpropionate, prepared as described in Example 9a, (7.67 g, 33.5 mmol) and methyl glycolate (3.93 g, 33.3 mmol) in 125 mL of ethyl ether containing 0.125% tert-butylbenzene was added to 9.0 g Lipase AK and the reaction mixture was agitated on an orbital shaker for 4 d. The enzyme powder was removed by filtration, the solvent was removed, and a portion of the resulting residue was partially purified by flash chromatography (ethyl acetate/hexane, 10/90) to give a mixture of 2-chloroethyl 2-hydroxy-3-phenylpropionate and the title compound as an oil. The partially purified mixture was separated by flash chromatography (CH$_2$Cl$_2$) to give the title compound: $^1$H NMR δ1.27 (d, 6H, J=6.3 Hz), δ2.77 (d, 1H, J=6.1 Hz), δ3.00 (dd, 1H, J=7.7 Hz and 14.0 Hz), δ3.23 (dd, 1H, J=4.1 Hz and 14.0 Hz), δ4.55 (ddd, 1H, J=4.1 Hz, 6.1 Hz, and 7.7 Hz), δ4.61 (d, 1H, J=15.7 Hz), δ4.70 (d, 1H, J=15.7 Hz), δ5.10 (m, 1H, J=6.3 Hz), 7.2-7.3 (m, 5H); $^{13}$C NMR 21.6, 40.5, 61.4, 69.5, 71.3, 126.7, 128.3, 129.4, 136.5, 166.6, 173.4 ppm.

Example 10

Chemical Synthesis of 2-Methoxy-2-oxoethyl Lactate

Tetramethylammonium lactate dihydrate was prepared by the addition of tetramethylammonium hydroxide (25% in methanol) to an equivalent amount of lactic acid (85% aqueous solution) with cooling on ice followed by solvent removal and the addition of sufficient water to form the dihydrate.

Methyl bromoacetate (4.73 mL, 50 mmol) was added to a stirring solution of tetramethylammonium lactate dihydrate (11.0 g, 55 mmol) in 20 mL dimethylformamide at room temperature. Tetramethylammonium bromide separated from the reaction mixture as a white solid and the title compound was formed quantitatively within 60 min as determined by CG (Method A). The reaction mixture was filtered, the solids were washed with ethyl ether, and the combinated filtrate and ether solution was washed with 5% NaCl/5% NaHCO$_3$. Sufficient ethyl ether was added to effect rapid separation of the phases, the aqueous phase was extracted with CH$_2$Cl$_2$, and the organic phases were combined and dried with MgSO$_4$. The solvent was removed and the resulting residue was distilled under reduced pressure to give the title compound: b.p. 79° C./0.15 mm Hg.

Example 11

Chemical Synthesis of 2-Oxo-2-phenoxyethyl Lactate

Phenyl bromoacetate (45.0 g, 0.209 mol) was added to a stirring solution of tetramethylammonium lactate (40.7 g of an 88% aq soln, 1.05 eq) in 50 mL of dimethylformamide at room temperature. The resulting tetramethylammonium bromide which separated from the reaction mixture as a solid was removed by filtration and washed with ethyl acetate. The dimethylformamide and ethyl acetate solutions were combined and washed with a NaHCO$_3$/brine solution, the separated aqueous phase was extracted with CH$_2$Cl$_2$, and the organic phases were combined and dried with MgSO$_4$. The solvent was removed and the resulting residue was chromatographed on silica gel (ethyl acetate/hexane) to give the title compound (14.7 g, 31%): $^1$H NMR δ1.50 (d, 3H, J=7.0), δ3.12 (d, 1H, J=5.3), δ4.40-4.49 (m, 1H), δ4.87 (d, 1H, J=16.1), δ4.99 (d, 1H, J=16.2), d 7.09-7.40 (5H, phenyl); HRMS calcd for $C_{10}H_8O_5$TMS (M-CH$_3$) 281.0845, obsd 281.0856.

Example 12

Chemical Synthesis of Methyl 2-(2-Hydroxy-1-oxoethoxy)propionate

Tetramethylammonium hydroxide (25% in methanol) was added to a stirring solution of glycolic acid (3.8 g, 50 mmol) in 5 mL dimethylformamide cooled on ice until a pH of 7 was indicated by moistened pH paper. Methyl 2-bromopropionate (6.1 mL, 55 mmol) was added and the reaction was stirred at room temperature for 5 d. The reaction mixture was filtered, the solids were washed with ethyl ether, and the combined filtrate and ether solution was washed with 5% NaCl/5% NaHCO$_3$. Sufficient ethyl ether was added to effect rapid separation of the phases, the aqueous phase was extracted with CH$_2$Cl$_2$, and the organic phases were combined and dried with MgO$_4$. The solvent was removed and the resulting residue was distilled under reduced pressure to give the title compound: b .p. 64° C./0.05 mm Hg; $^1$H NMR $\delta$1.53 (d, 3H, J=7.2 Hz), $\delta$2.78 (bs, 1H), $\delta$3.77 (s, 3H), $\delta$4.24 (d, 1H, J=17.4 Hz), $\delta$4.31 (d, 1H, J=17.4 Hz), $\delta$5.22 (q, 1H, J=7.1 Hz), HRMS calcd for $C_6H_9O_5Tms$ (M-CH$_3$) 219.0688, obsd 219.0708.

As many different embodiments of this invention may be made without departing from the spirit and scope thereof, it is to be understood that this invention is not limited to the specific embodiments exemplified except as defined by the appended claims.

We claim:

1. A process for preparation of a compound of the formula:

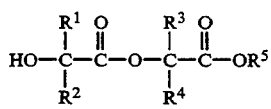
Ia wherein:

$R^1$, $R^2$, $R^3$, and $R^4$ are selected from the group consisting of hydrogen, alkyl, aryl, alkaryl, aralkyl wherein said alkyl, aryl, alkaryl, aralkyl optionally have one or more branched chain, unsaturated chain, halogen, nitrile, ketone or ether substitutions and $R^5$ is selected from the group consisting of alkyl, aryl, alkaryl and aralkyl wherein said alkyl, aryl, alkaryl and aralkyl optionally have one or more branched chain, unsaturated chain, halogen, nitrile or ether substitutions and wherein $R^1$ and $R^2$ are not equal to $R^3$ and $R^4$; comprising reacting a compound of formula:

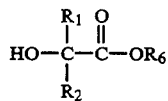
III with a compound of formula:

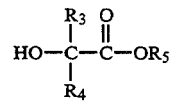
IV wherein:

$R^1$, $R^2$, $R^3$, $R^4$ and $R^5$ are as defined above and $R^6$ is selected from the group consisting of alkyl, aryl and aralkyl, wherein said alkyl, aryl and aralkyl optionally have one or more branched chain, unsaturated chain, or halogen, ether or nitrile substitutions in the presence of an enzyme selected from carboxyesterases or carboxyamidases and in the presence of an organic solvent.

2. The process of claim 1 wherein the ester moieties of structures III and IV are selected from the group consisting of phenyl, substituted phenyl, —CH$_2$CCl$_3$, —CH$_2$CF$_3$, CH$_2$C$_3$XBONDCH, —CH$_2$CH$_2$F, —CH$_2$CH$_2$Cl, —(CH$_2$)$_n$CH$_3$ where n is 0 to 7, —CH(CH$_3$)$_2$, and —C(CH$_3$)$_3$.

3. The process of claim 1 wherein the enzyme is immobilized on a solid support.

4. The process of claim 1, wherein the solvent is selected from aliphatic hydrocarbons, aromatic hydrocarbons, ethers, halogenated hydrocarbons, nitriles, pyridine and dimethylformamide.

5. The process of claim 4 wherein the solvent is ethyl ether.

6. The process of claim 1 wherein the enzyme is not soluble in the solvent.

7. The process of claim 1 wherein the enzyme is soluble in the solvent.

8. The process of claim 1 wherein the reactants III and IV are present in a ratio of from 1:1 to 1:10.

9. The process of claim 8 wherein the ratio of reactant III to reactant IV is from 1:1 to 1:2.

10. The process of claim 1 wherein the reaction is terminated by filtering the reactants.

11. The process of claim 1 conducted within a temperature range of 0° C. to 70° C.

12. The process of claim 1 wherein the enzyme is selected from lipases, proteases and esterases or a mixture of two or more thereof.

* * * * *